United States Patent
Vanhoutte et al.

(10) Patent No.: US 7,468,434 B2
(45) Date of Patent: Dec. 23, 2008

(54) DIAZENE-BRIDGE CROWN ETHER LITHIUM COMPOUNDS AND METHODS FOR THEIR USE

(75) Inventors: Paul Michel Georges Vanhoutte, Hong Kong (HK); Chi-Ming Che, Hong Kong (HK); Kwok-Fai So, Pokfulam (HK); Iona Hiu Tung Sham, Chai Wan (HK)

(73) Assignee: The University of Hong Kong, Hong Kong (CN)

( * ) Notice: Subject to any disclaimer, the term of this patent is extended or adjusted under 35 U.S.C. 154(b) by 138 days.

(21) Appl. No.: 11/313,513

(22) Filed: Dec. 21, 2005

(65) Prior Publication Data

US 2007/0298127 A1 Dec. 27, 2007

Related U.S. Application Data

(60) Provisional application No. 60/638,100, filed on Dec. 22, 2004.

(51) Int. Cl.
*C07D 225/00* (2006.01)

(52) U.S. Cl. ............... 540/450; 540/467; 540/468; 540/469

(58) Field of Classification Search ............... None
See application file for complete search history.

(56) References Cited

OTHER PUBLICATIONS

Huang et al. "Support of Retinal Ganglion Cell Survival and Axon Regeneration by Lithium through a Bcl-2 Dependent Mechansim", Investigative Ophthalmology & Visual Science, 44(1), p. 347-354. Jan. 2003.*

Birch, N.J., "Biomedical Uses of Lithium," Uses of Inorganic Chemistry in Medicine, ed. Farrell, N.P., 1999, 11-25.

Birch, N.J., "Inorganic Pharmacology of Lithium," Chem. Rev., 1999, 1659-2682, vol. 99.

Blank, M. et al., "Photoregulated Ion Binding," Science, 1981, 70-72, vol. 214.

Cheung, Z.H. et al., "Enhanced Survival and Regeneration of Axotomized Retinal Ganglion Cells by . . . ," Journal of Neurotrauma, 2002, 369-378, vol. 19, No. 3.

Cho, K.S. et al., "Ciliary Neurotrophic Factor Promotes the Regrowth Capacity but not the Survival of Intraorbitally . . . ," Neuroscience, 1999, 623-628, vol. 94, No. 2.

Cho, K.S. et al., "Differential Effects of Intravitreal Optic Nerve and Sciatic Nerve Grafts on the Survival . . . ," Journal of Neurocytology, 2001, 983-991, vol. 30.

Garcia-Valenzuela, E. et al., "Programmed Cell Death of Retinal Ganglion Cells Durig Experimental Glaucoma," Exp. Eye Res., 1995, 33-44, vol. 61.

(Continued)

*Primary Examiner*—Michael G Hartley
*Assistant Examiner*—Nissa M Westerberg
(74) *Attorney, Agent, or Firm*—Robert D. Katz; Cooper & Dunham LLP

(57) ABSTRACT

This invention provides a method for treating an eye disease in a patient comprising: providing a photosensitive prodrug that releases upon exposure to light an active ingredient to treat the eye disease; administering the prodrug in a pharmaceutically accepted vehicle to the subject, and exposing the eye of the subject to an external light source to cause the prodrug to release the active ingredient. This invention also provides a composition for the treatment of glaucoma, comprising a compound containing a lithium ion-chelated in a crown ether- or aza-crown ether-containing chromene or diazene derivative and a pharmaceutically acceptable carrier.

8 Claims, 6 Drawing Sheets

OTHER PUBLICATIONS

Ikeda, T. et al., "Optical Switching and Image Storage by Means of Photochromic Liquid Crystals," Mol. Cryst. and Liq. Cryst., 2000, 1-13, vol. 347.

Ji, J-Z. et al., "CNTF Promotes Survival of Retinal Ganglion Cells after Induction of Ocular Hypertension in Rats . . . ," Euro. J. Neurosci., 2004, 265-272, vol. 19.

Laquis, S. et al., "The Patterns of Retinal Ganglion Cell Death in Hypertensive Eyes," Brain Research, 1998, 100-104, vol. 784.

Leske, M.C., "The Epidemiology of Open-Angle Glaucoma: A Review," American Journal of Epidemiology, 1983, 166-191, vol. 118, No. 2.

Levy, D., "Recent Applications of Photochromic Sol-Gel Materials," Mol. Cryst. Liq. Cryst., 1997, 31-39, vol. 297.

Lorincz, E. et al., "Polarization Holographic Data Storage Using Azobenzene Polyester as Storage Material," 2003, 34-44, vol. 4991.

Lu, Q. et al., "c-Jun Expression in Surviving and Regenerating Retinal Ganglion Cells . . . ," Investigative Opththalmology & Visual Science, 2003, 5342-5348, vol. 44, No. 12.

Matsui, F. et al., "Application of Photochromic 5-Dimethylaminoindolylfulgide to Photon-Mode Erasable Optical Memory Media . . . ," Chemistry Letters, 1994, 1869-1872.

McKinnon, S.J., et al. "Baculoviral IAP Repeat-Containing-4 Protects Optic Nerve Axons in a Rat Glaucoma Model," Molecular Therapy, 2002, 780-787, vol. 5, No. 6.

Mittag, T.W. et al., "Retinal Damage after 3 to 4 Months to Elevated Intraocular Pressure in a Rat . . . ," Invest. Ophthamol. & Vis. Sci., 2000, 3451-3459, vol. 41, No. 11.

Morrison, J.C. et al., "A Rat Model of Chronic Pressure-Induced Optic Nerve Damage," Exp. Eye. Res., 1997, 85-96, vol. 64.

Natansohn, A. and Rochon, P., "Photoinduced Motions in Azobenzene-Based Amorphous Polymers . . . ," Adv. Mater., 1999, 1387-1391, vol. 11, No. 16.

Nunzi, J.M. et al., "Limits of Use of Polymer Thin-Films for Spatial Light Modulation," SPIE, 138-144, vol. 2969.

Osborne, N.N. et al., "Ganglion Cell Death in Glaucoma: What Do We Really Know?" Br. J. Ophthalmol., 1999, 980-986, vol. 83.

Quigley, H.A. and Green, W.R., "The Histology of Human Glaucoma Cupping and Optic Nerve Damage . . . ," Ophthalmology, 1978, 1803,-1830, vol. 86.

Rompotis, S. et al., "Determination of Valproic Acid in Human Plasma by HPLC . . . ," Journal of Liquid Chromatography & Related Technologies, 2002, 2833-2847, vol. 25, No. 18.

Sawada, A. and Neufeld, A.H., "Confirmation of the Rat Model of Chronic, Moderately Elevated Intraocular Pressure," Exp Eye Res., 1999, 525-31, vol. 69.

Shanzer, A. et al., "Lipophilic Lithium Ion Carriers," J. Am. Chem. Soc., 1983, 3815-3818, vol. 105.

Shinbo, K. et al., "In Situ Investigations on the Preparations of Layer-by-Layer Films Containing . . . ," Materials Science and Engineering C, 2002, 319-325, vol. 22.

Shinkai, S. et al., "Photoresponsive Crown Ethers. 1. Cis-Trans Isomerism of Azobenzene as a Tool to Enforce . . . ," J. Am. Chem. Soc., 1980, 5860-5865, vol. 102.

Shinkai, S. et al. "Photoresponsive Crown Ethers. 2. Photocontrol of Ion Extraction and Ion Transport by a Bis(Crown Ether) . . . ," J. Am. Chem. Soc., 1981, 111-115, vol. 103.

Siu, A.W. et al., "Total Retinal Nitric Oxide Production is Increased in Intraocular Pressure-Elevated Rats," Exp. Eye Res., 2002, 401-406, vol. 75.

Stauffer, M.T. et al., "Optical Control Over Pb2+ Binding to a Crown Ether-Containing Chromene," Chem. Commun., 1997, 287-288.

Ueda, J. et al., "Experimental Glaucoma Model in the Rat Induced by Laser Trabecular Photocoagulation . . . ," Jpn. J. Ophthalmol., 1998, 337-344, vol. 42.

Woldemussie, E. et al., "Neuroprotection of Retinal Ganglion Cells by Brimonidine in Rats with Laser-Induced . . . ," Invest. Ophthalmol. & Vis. Sci., 2001, vol. 42, No. 12.

Woldemussie, E. et al., "Neuroprotective Effect of Memantine in Different Retinal Injury Models in Rats," Journal of Glaucoma, 2002, 474-480, vol. 11.

Yoon, H.C. et al., "Fabrication of Azobenzene-Terminated Dendrimers and Application to Photoswitching Devices," Synthetic Metals, 2003, 1427-1428, vol. 137.

You, S-W. et al., "Axonal Regenerationof Retinal Ganglion Cells After Optic Nerve Pre-Lesions . . . ," Visual Neuroscience, 2002, 661-668, vol. 19.

Zhang, X.H. et al., "A New Family of Red Dopants Based on Chromene-Containing Compounds for Organic . . . ," Chem. Mater., 2001, 1565-1569, vol. 13.

Zhang, Z. et al., "A Water-Soluble Azobenezene Cross-Linker for Photocontrol of Peptide Conformation," Bioconjugate Chem., 2003, 824-829, vol. 14.

* cited by examiner

X = H or O^tBu

DIAZENE-BRIDGE CROWN ETHER LITHIUM COMPOUNDS AND METHODS FOR THEIR USE

This application claims priority of U.S. Provisional Application No. 60/638,100, filed Dec. 22, 2004, the contents of which are hereby incorporated by reference into this application.

Throughout this application, various publications are referenced. Full citations for these publications may be found immediately preceding the claims. The disclosures of these publications are hereby incorporated by reference into this application in order to more fully describe the state of the art as of the date of the invention described and claimed herein.

BACKGROUND OF THE INVENTION

Glaucoma is a human disorder marked by progressive loss of vision; it is one of the leading causes of irreversible blindness in the world. The World Health Organization (WHO) estimated that the total number of glaucoma cases was 105 million people in 1977. In China alone, Foster and Johnson in 2001 reported that the disease afflicted an estimated 9.4 million people (for age group 40 years and older), of which 5.2 million (55%) were blind in at least one eye.

One hypothesis underlying the loss of retinal ganglion cells in glaucoma is the induction of cell death genes either because of blockage of retrograde axonal transport or increase production of toxic material in the eye. Thus, the objective of the experiment is to make use of our established animal model of glaucoma with increased intraocular pressure by blocking the outflow of the aqueous humour with laser photocoagulation of the episcleral and limbal veins. In addition, our previous work has shown that lithium chloride is a neuroprotective factor in the eye. LiCl or other photosensitive lithium compounds has been injected into rats to examine their role in protecting the death of retinal ganglion cells in the rat glaucoma model. This model is useful in studying the mechanism of lithium on preventing cell death in glaucoma. The photosensitive lithium compounds have much lower side effect since it would only be activated inside the eye, so this approach is potentially be useful for patients with the glaucoma disease.

The major pathological features of glaucoma are the death of retinal ganglion cells (RGSs), and cupping and atrophy of optic nerve head leading to the loss of vision. (Leske, 1983; Osborne, 1999; Quigley, 1979). Glaucomatous optic neuropathy reduces vision gradually and often without symptoms. Many patients are unaware of the pathological condition during the early stage of glaucoma until it progresses into complete blindness. Similar to other neurons in the central nervous system (CNS), RGCs do not generally regenerate once they are damaged. However, progressive visual field loss in many types of eye diseases affecting the RGC axons can be prevented if it is treated at an early stage. Therefore, it is important to prevent the degeneration of RGCs in any kind of optic neuropathy.

So far, there seems to be no adequate therapy for protecting against the death of the retinal ganglion cells in glaucoma. The current clinical treatment for glaucoma is to delay the progressive loss of RGCs with the few neuroprotective agents available, while much research effort is directed towards the prevention of RGC death and apoptosis in various optic neuropathy conditions. Knowledge of the mechanisms responsible for the various optic neuropathy conditions such as glaucomatous optic neuropathy, ischemic optic neuropathy, inflammatory optic neuropathy, compressive optic neuropathy and traumatic optic neuropathy, is critical in the development of new treatments for them. A number of animal glaucoma models have been established to mimic the pathogenic conditions including optic nerve transection (Cheung, 2002; Cho, 1999; Cho, 2001; Lu, 2003; You, 2002), and ocular hypertension (Garcia-Valenzuela, 1995; Laquis, 1998; McKinnon, 2002; Mittag, 2000; Morrison, 1997; Sawada, 1999; Ueda, 1998). The present inventors have developed an ocular hypertensive model of photocoagulation to the limbal and episcleral veins using argon laser (Ji, 2004; WoldeMussie, 2001; WoldeMussie, 2002).

Lithium chloride is a common drug for the clinical treatment of mania and depression. Recent studies suggest that it has a neuroprotective effect on the injured CNS via a number of intracellular signaling pathways including upregulation of the anti-apoptotic gene Bcl-2, and inhibition of glycogen synthase kinase-3β (GSK-3β). Lithium-induced Bcl-2 upregulation plays a pivotal role in neuroprotection against glutamate excitotoxicity and supporting the intrinsic growth potential of injured axons. GSK-3β is a key downstream target of the PI3-kinase/Akt signaling pathway that regulates apoptosis in the injured CNS. Using the ocular hypertensive model to study the pathophysiology of glaucoma, So and his colleagues have shown that lithium chloride could prevent degeneration of RGC (Ji, 2002).

Despite the immense therapeutic value of lithium, there are serious long-term associated complications. These include severe, coarse tremor, exacerbation of dermatological disorders, leukocytosis, hypothyroidism, hypoparathyroidism as well as disruption of kidney function (Birch, 1999 and 1999). The undesirable side effects are possibly caused by slow penetration of lithium through the blood-brain barrier and across other membranes, resulting in delayed onset of action which necessitates the high dosage (Shanzer, 1983). Accordingly, it is an object of the current invention to provide new treatments and methods utilizing the novel use of photosensitive compounds to treat various diseases.

Photosensitive systems, including those with photochromic units such as diazene or chromene, have been widely used in unrelated fields such as optical recording and information storage devices (Ishige, 1980; Loerincz, 2003; Matsui, 1994), light-controlling media (Levy, 1997; Natansohn, 1999; Nunzi, 1996), liquid crystal displays and organic light-emitting devices (Shinbo, 2002; Zhang X. H., 2001), molecular switches (Ikeda, 2000; Yoon, 2003; Zhang Zhihua, 2003) as well as security inks for anti-forgery trademarks (Fan, 1997). More particularly, the photoresponsive system described in this invention includes a photosensitive moiety attached to or incorporated in a chelating moiety; such photoresponsive chelators have been used for sensing (Alward, 1998; Rompotis, 2002) and extraction of metal ions (Alward, 1998; Blank, 1981; Shinkai, 1980; Shinkai, 1981).

SUMMARY OF THE INVENTION

This invention provides a method for treating an eye disease in a subject comprising: providing a photosensitive prodrug that releases upon exposure to light an active ingredient to treat the disease, administering the prodrug in a pharmaceutically acceptable carrier to the subject, and exposing the eye of the subject to an external light source to cause the prodrug to release the active ingredient.

The invention also provides a method for protecting the degeneration of retinal ganglion cells in a subject comprising (a) providing a photosensitive prodrug that releases upon exposure to light an active ingredient to treat the eye disease; (b) administering the prodrug in a pharmaceutically acceptable carrier to the eye of the subject; and (c) exposing the eye of the subject to an external light source to cause the prodrug to release the active ingredient.

The invention further provides a compound having one of the following structures:

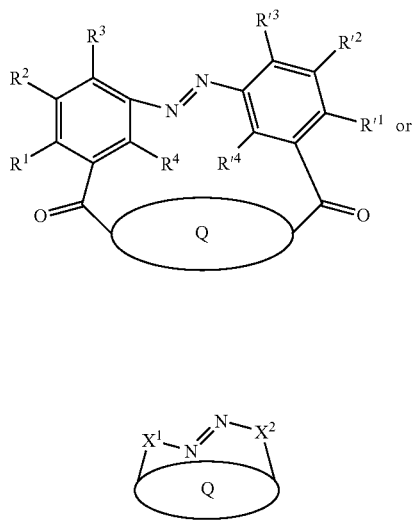

wherein Q is a crown ether or an aza-crown ether of any size; wherein $R^1$, $R^2$, $R^3$, $R'^1$, $R'^2$, $R'^3$, $X^1$ and $X^2$ are the same or different, and are each selected from the group consisting of a whole or part of a phenyl ring or substituted phenyl ring, a hydrogen; a halogen, a hydroxyl group, as well as unsubstituted or substituted lower alkyls, cycloalkyls, aryl, acyl, alkoxy, acylamino, arakyl cyanocarboxyl, thio, vinyl, stryryl, alkoxycarbonyl, carbamoyl, aminocarbonyl, phenoxycarbonyl, with the substituents being the listed above metals, hydrogen, halogens and hydroxyl groups, as well as recognized donor and acceptor groups; and wherein the substituents may combine together to form a substituted or unsubstituted, saturated or unsaturated ring with any number of members.

DETAILED DESCRIPTION OF THE PREFERRED EMBODIMENTS

Definitions

Figure 1:
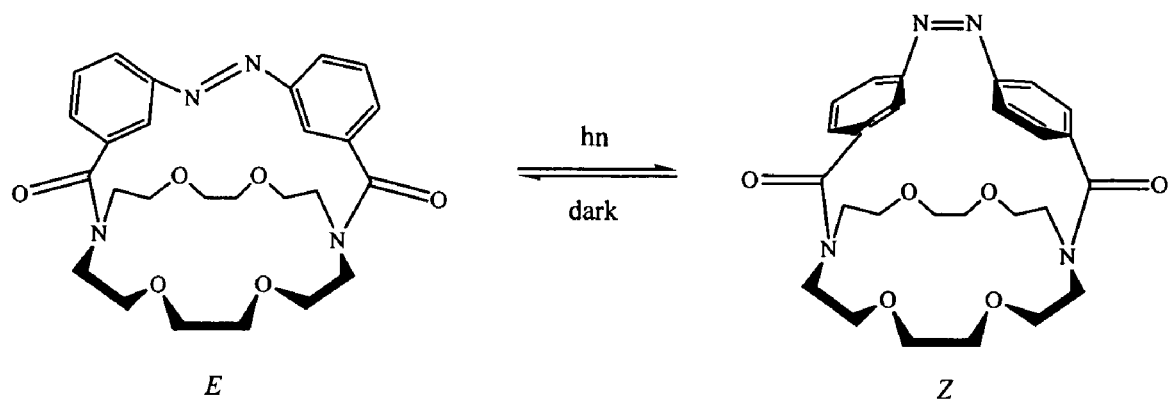
FIG. 1 Photosensitive lithium ionophore (1)/Ligand (1), a diazene-bridged crown ether which binds lithium ion in the dark and releases lithium ion on irradiation (Shinkai, 1980).

As used herein, "administering" an agent can be effected or performed using any of the various methods and delivery systems known to those skilled in the art. The administering can be performed, for example, intravenously, via cerebrospinal fluid, orally, nasally, via implant, transmucosally, transdermally, intramuscularly, and subcutaneously.

As used herein, "pharmaceutically acceptable carrier" shall mean any of the various carriers known to those skilled in the art.

The following delivery systems, which employ a number of routinely used pharmaceutical carriers, are only representative of the many embodiments envisioned for administering the instant compositions.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents and coating agents.

As used herein, "effective amount" means an amount sufficient to treat a patient afflicted with an eye disease or a complication thereof.

As used herein, "treating" a disorder shall mean slowing, stopping or reversing the progression of the disease.

PREFERRED EMBODIMENTS

To illustrate the present invention, phototherapy for glaucoma employing lithium is used as an example, but should not be construed as limited to treatments of glaucoma or those employing lithium. The aim is to achieve controlled delivery of lithium for ocular treatment. An intact and stable lithium prodrug, which includes a drug delivery system carrying a lithium ion, is designed such that it is an inactive form of lithium in the dark but releases the active lithium ion upon irradiation of UV or visible light. The lithium ion can be encapsulated by, or preferably chelated to the drug delivery system in the dark. The lithium prodrug can be present throughout the body in an inert form, and only has therapeutic actions in the eyes where there is direct contact with external light. This approach can lower the active dosage and minimize the undesirable side effects currently hindering available treatments. The prodrug can be delivered orally, topically or by injection.

The drug delivery system comprises of a photosensitive moiety attached to or incorporated in a chelating moiety. Radiation induced change in the photosensitive moiety can reversibly or irreversibly affect the binding property of the chelating moiety. For example, there can be two kinds of changes in the drug delivery system upon irradiation:
1. The photosensitive moiety undergoes isomerization and causes an overall conformational change in the drug delivery system, thereby handicapping the binding ability of the chelating moiety; or
2. The photosensitive moiety shifts electron density out of the chelating moiety, thus causing the chelating moiety to lose its binding ability.

These examples are set forth to illustrate the concept, but are not intended to limit this invention in any way. The system can be designed such that the photosensitive moiety can reversibly or irreversibly affect the binding property of the chelating moiety upon exposure to any type of radiation.

Preferably, the chelating moiety is a crown ether or one of its derivatives, or an aza-crown ether or one of its derivatives. Crown ethers or aza-crown ethers or their derivatives of different ring size can be chosen for selective binding, e.g. of different metal ions. The choice of the chelating moiety, however, is not limited to cyclic compounds.

Preferably, the photosensitive moiety is a conjugated molecule which is capable of altering the electron density of the crown ether derivative, or a photoisomer which is capable of changing the ring size of the crown ether derivative thereby affecting its selective binding ability. The photosensitive moiety does not necessarily have to be conjugated, does not have to possess the ability to alter the electron density of the chelating moiety, nor does it have to be able to undergo photoisomerization.

For this purpose, the drug delivery systems are conveniently referred to as photosensitive lithium ionophores (X) or Ligand (X) hereinafter. The prodrugs, which contain a lithium ion chelated in photosensitive lithium ionophore (X)/Ligand (X), are conveniently referred to as Lithium Complex (X) hereinafter.

EXAMPLE 1

Photosensitive Lithium Ionophore (1)/Ligand (1)

Figure 2:
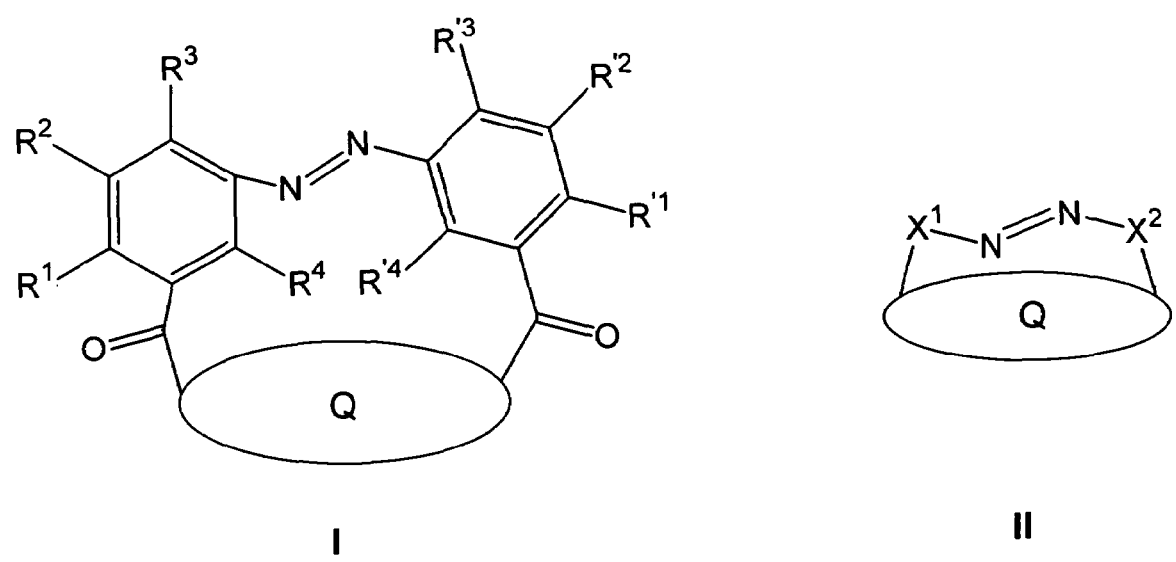
FIG. 2 Systems containing different diazenes or diaza-crown ethers of different sizes and derivatives of diazene-bridged crown ethers seen to function in the same way as photosensitive lithium ionophore (1)/Ligand (1).

Photosensitive lithium ionophore (1)/Ligand (1) is a diazene-bridged crown ether (Shinkai, 1980), where the photosensitive moiety is a diazene or an azo-benzene derivative and the chelating moiety is a diaza-18-crown-6 ether. The diazene moiety adopts the E or trans conformation in the dark, and the crown ether chelates to a lithium ion. On exposure to near-UV light for several seconds, the diazene moiety undergoes photoisomerization to adopt the Z or cis conformation, causing a ring expansion of the crown ether moiety and thereby releasing the lithium ion (FIG. 1). Other similar systems containing different diazenes or crown ethers or diaza-crown ethers of different sizes or derivatives of diazene-bridged crown ethers are seen to function in the same way as photosensitive lithium ionophore (1)/Ligand (1) (FIG. 2).

Derivatives of diazene-bridged crown ethers (FIG. 2) may include a crown ether or aza-crown ether of any size and $R^1$-$R^3$ and/or $R^{1'}$-$R^{3'}$ and/or $X^1$ and/or $X^2$ groups on the diazene, wherein $R^1$, $R^2$, $R^3$, $R^{1'}$, $R^{2'}$, $R^{3'}$, $X^1$ and $X^2$ are the same or different, and are each selected from the group consisting of: a whole or part of a phenyl ring or substituted phenyl ring; a hydrogen; a halogen, a hydroxyl group; as well as unsubstituted or substituted lower alkyls, cycloalkyls, aryl, acyl, alkoxy, acylamino, arakyl cyanocarboxyl, thio, vinyl, stryryl, alkoxycarbonyl, carbamoyl, aminocarbonyl, phenoxycarbonyl, with the substituents being the listed above metals, hydrogen, halogens and hydroxyl groups, as well as recognized donor and acceptor groups; wherein the substituents may combine together to form a substituted or unsubstituted, saturated or unsaturated ring with any number of members.

EXAMPLE 2

Photosensitive Lithium Ionophore (2)

Figure 3:
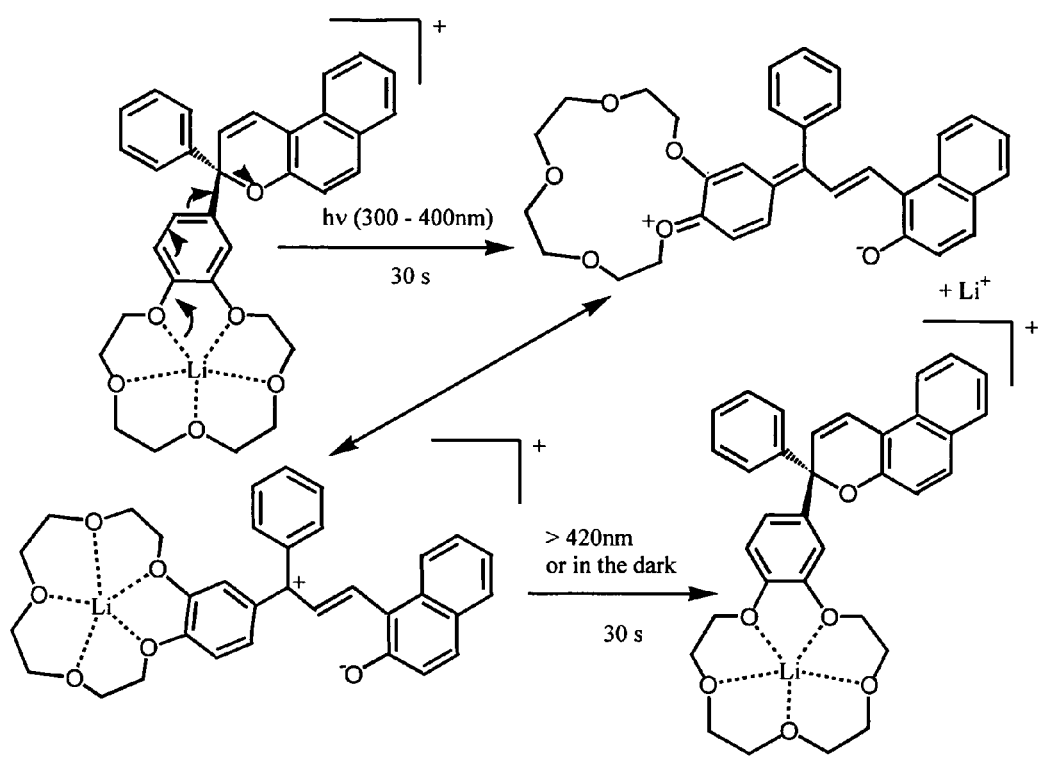
FIG. 3 Photosensitive lithium ionophore (2)/Ligand (2), a crown ether containing chromene which binds lithium ion in the dark and releases lithium ion on irradiation (Stauffer, 1997).
Figure 4:
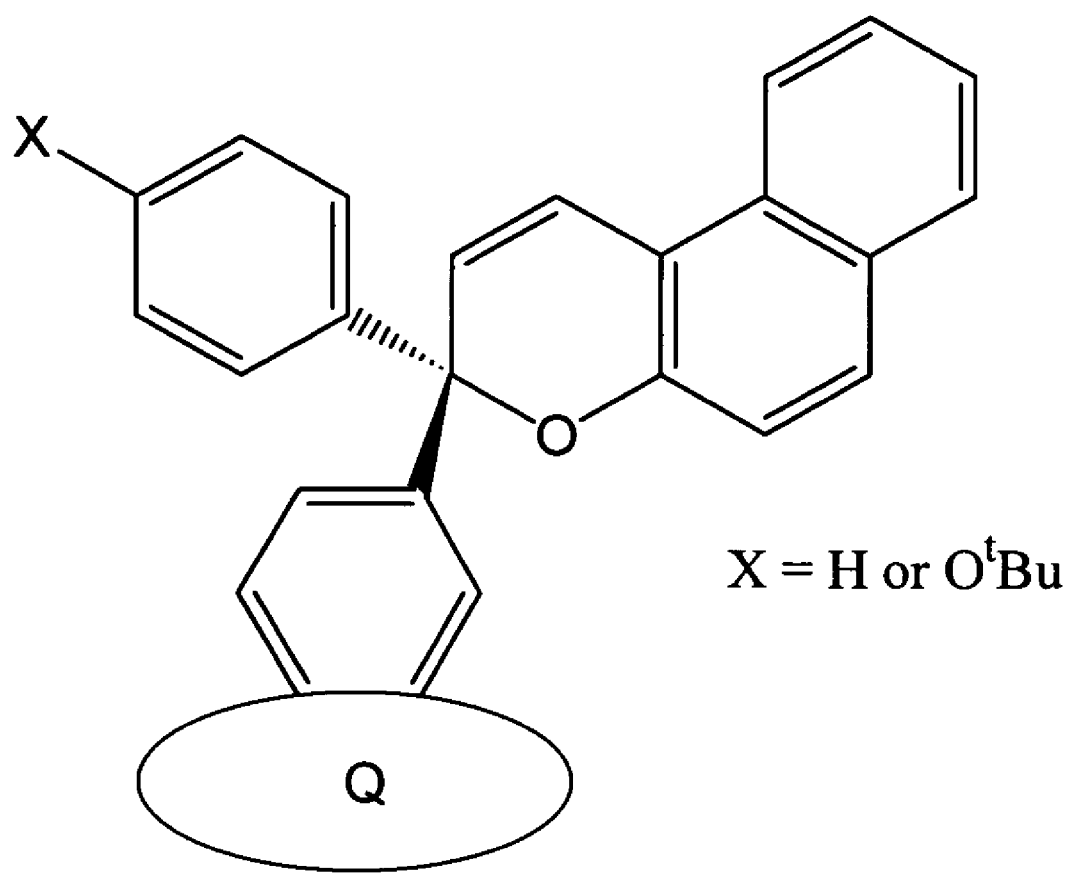
FIG. 4 Derivatives of chromene systems containing crown ethers of different sizes seen to function in the same way as photosensitive lithium ionophore (2)/Ligand (2).

Photosensitive lithium ionophore (2)/Ligand (2) is a crown ether containing chromene (Stauffer, 1997), where the photosensitive moiety is a chromene derivative and the chelating moiety is a benzo-15-crown-5 ether. In the dark, the benzo-crown ether chelates to a lithium ion. On exposure to near-UV light for seconds to minutes, the chromene moiety withdraws electron density from the benzo-crown ether and causes the crown to lose its metal ion binding ability (FIG. 3). Other derivatives of chromene systems containing crown ethers of different sizes are seen to function in the same way as photosensitive lithium ionophore (2)/Ligand (2) (FIG. 4).

This invention provides a method for treating an eye disease in a patient comprising providing a photosensitive prodrug that releases upon exposure to light an active ingredient to treat the eye disease; administering the prodrug in a pharmaceutically accepted vehicle to the patient, and exposing the eye to an external light source to cause the prodrug to release the active ingredient.

This invention further provides the above method wherein the prodrug is present throughout the body in an inactive form, and only has therapeutic actions in the eyes where there is contact with external light.

This invention further provides the above method wherein the method is for treatment of glaucoma, or wherein the prodrug is a lithium prodrug. The lithium prodrug may include a drug delivery system comprising a photosensitive moiety attached to or incorporated in a chelating moiety for lithium.

This invention further provides the above method wherein a lithium ion in the lithium prodrug is chelated in the dark and is released on irradiation. The prodrug may comprise a photosensitive moiety and a chelating moiety, the photosensitive moiety affecting the binding ability of the chelating moiety over lithium ion on irradiation irreversibly or reversibly. The prodrug further comprises a releasable active agent. The releasable active agent may be lithium. The lithium may be released upon the exposure to light. The photosensitive moiety may be attached to, or incorporated into the chelating moiety. The photosensitive moiety may irreversibly or reversibly affect the binding properties of the chelating moiety. The photosensitive moiety may be a diazene or a derivative thereof or a chromene or a derivative thereof. The chelating moiety may be a crown ether or a derivative thereof, an aza-crown ether or a derivative thereof.

The photosensitive moiety may undergo isomerization on irradiation, thereby changing the conformation and size of the chelating moiety and causing the chelating moiety to lose its ability to bind lithium ion. The photosensitive moiety may also withdraw electron density from the chelating moiety on irradiation, thereby causing the chelating moiety to lose its ability to bind lithium ion.

The invention further provides the above method wherein the eye disease is glaucoma, the prodrug releases lithium, and the prodrug is administered to the patient by injection.

The invention further provides the above method wherein the prodrug releases lithium from a crown ether or aza-crown ether containing chromene or diazene derivative.

The invention further provides the above method wherein the prodrug remains inactive in the body outside of the eye of the patient.

The invention further provides the above method wherein a lithium ion is chelated to a crown either or aza-crown ether derivative to form a chelated lithium containing chelated moiety that releases lithium upon exposure to light.

The invention further provides the above method wherein a lithium ion is reversibly bound to a crown ether or aza-crown ether containing diazene or chromene derivative to form a lithium releasing chromene or diazene compound, and the lithium is released upon exposure of the eye of the patient to light.

The invention further provides the above method wherein the photosensitive moiety undergoes isomerization on irradiation, thereby changing the conformation and/or size of the chelating moiety and causing the chelating moiety to lose its ability to bind lithium ion.

The invention further provides the above method wherein the photosensitive moiety withdraws electron density from the chelating moiety on irradiation, thereby causing the chelating moiety to lose its ability to bind lithium ion.

The invention further provides a composition for the treatment of glaucoma, comprising an injectable compound containing a lithium ion-diazene or chromene derivative where the lithium ion is chelated by a crown ether- or aza-crown ether-containing compound.

The invention further provides a composition for the treatment of glaucoma comprising a photosensitive moiety including a lithium ion bound to a chromene or diazene derivative through a crown ether or aza-crown ether moiety in a pharmaceutically acceptable carrier.

This invention also provides a method for treating an eye disease in a subject comprising administering an effective amount of a prodrug comprising a photosensitive moiety and a chelating moiety, whereby upon exposure to light, the photosensitive moiety affects the binding properties of the chelating moiety to the subject, and exposing the eye of the subject to light, thereby causing the release of an active agent capable of treating the eye disease. The eye disease may be glaucoma. The pharmaceutical composition may be administered intravenously, topically, orally, or directly to the eye of the subject. The subject may be human.

The invention further provides a composition for the treatment of glaucoma comprising an effective amount of a chelate formed from at least one lithium ion and a crown ether or aza-crown ether derivative where the lithium ion is chelated by a crown ether or aza-crown ether moiety.

Finally, the invention provides a kit for the treatment of glaucoma comprising a light protected ampule or syringe containing a composition for the treatment of glaucoma, comprising an injectable compound containing a lithium ion chelated in a crown ether- or aza-crown ether-containing chromene or diazene derivative and instructions for administration thereof to a patient.

The prodrug used in Examples 3 and 4 is Lithium Complex (1), where a lithium ion is chelated in photosensitive lithium ionophore (1)/Ligand (1). There is also a chloride anion which acts as the counteranion.

EXAMPLE 3

Glaucoma Model Treated with Lithium Complex (1)

The rats in this experiment were divided into three groups: the placebo group (12-hour exposure to light), the dark (24-hour darkness) group and the light (12-hour exposure to light) group. The rats in the dark group and the light group were given Lithium Complex (1) at a dose equivalent to 85 µg/kg LiCl by intraperitoneal injection continuously for 14 days. The rats were then sacrificed, the retinas were prepared and the retinal ganglion cells were counted.

Figure 5:
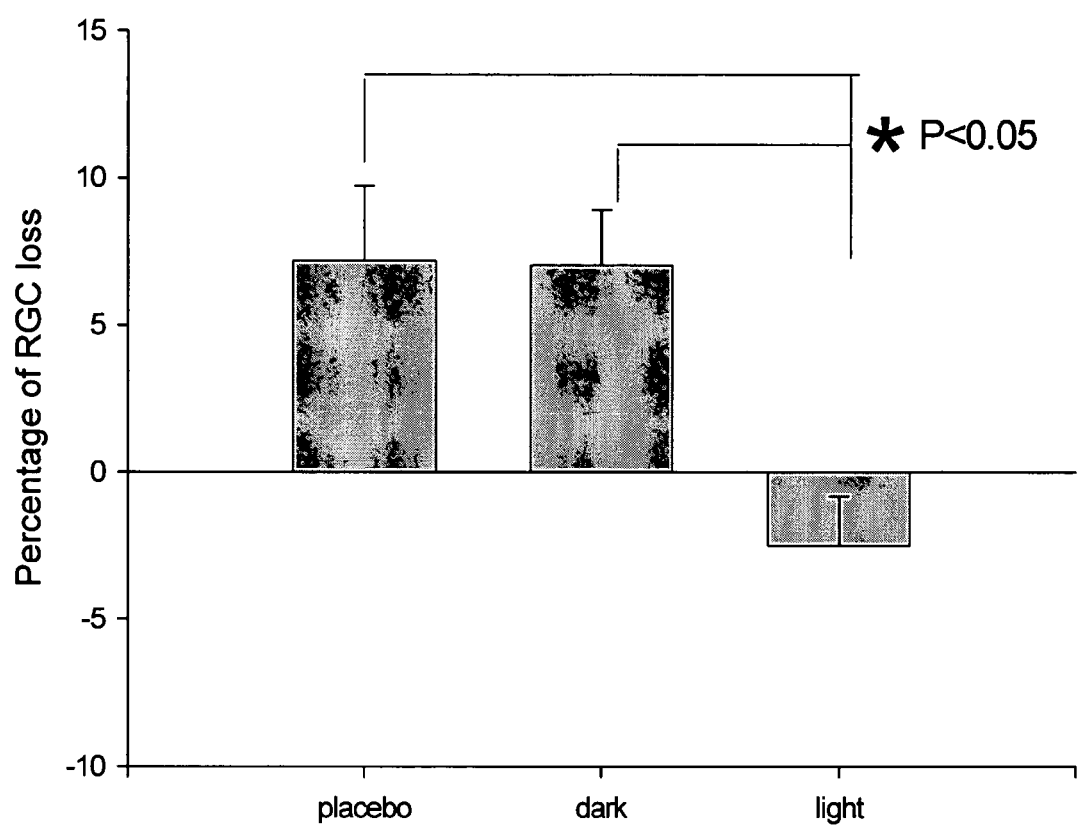
FIG. 5 Results showing percentage of retinal ganglion cell loss in three different groups of rats treated with Lithium Complex (1).

The results showed that both the placebo and the dark group have about 6-7% retinal ganglion cell loss, while the data of 12-hour-exposure-to-light group has a statistically significant difference to the above two groups (FIG. 5). There was no necessary retinal ganglion cell loss in the retinas in the 12-hour-exposure-to-light group. Therefore, neuroprotective effect was observed for treatment with Lithium Complex (1) in the light group.

EXAMPLE 4

Glaucoma Model Treated with 1/10 Dose of Lithium Complex (1)

This experiment included an extra group, the 1/10 dosage group, in addition to the three groups mentioned in Example 3. The rats in the 1/10 dosage group were given Lithium Complex (1) at a dose equivalent to 8.5 µg/kg LiCl, 1/10 of the original dose, and is exposed to light for 12 hours under the same conditions as the light group in Example 3.

Figure 6:
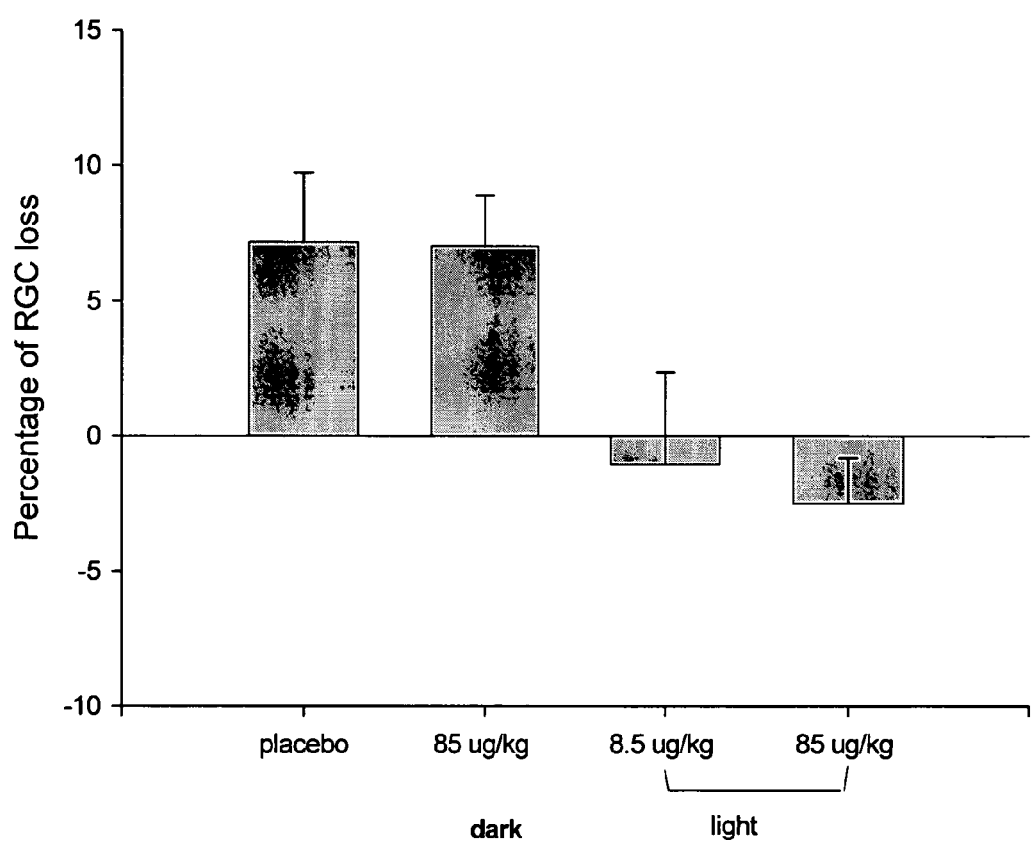
FIG. 6 Results showing percentage of retinal ganglion cell loss in the dosage experiment employing Lithium Complex (1).

The results showed that the 1/10 dosage group exhibited a similar neuroprotective effect as the light group in Example 3. There was, statistically, no significant difference on the neuroprotective effect between the 1/10 dosage group and the light group using the original dosage (FIG. 6). The 1/10 dosage group also did not necessarily show retinal ganglion cell loss in the retinas.

Experimental Details

Glaucoma Model in SD Rats and Death of Retinal Ganglion Cells

Adult female SD rats weighting 250-300 g are used. All animals are anaesthetized with xylazine/ketamine mixture or pentobarbitone for all operations.

Experimental glaucoma is induced in the right eye of each animal and the left eye is used as control. The episcleral and limbal veins of the right eye is photocoagulated (Siu et al., 2002; Ji et al. 2003) using an Argon laser (Coherent, power, 1V; spot, 50-100 µm and duration, 0.1 s). About 15-20 spots on two episcleral veins and 60 spots around the limbal veins are applied. A second laser treatment in the same setting is applied 7 days later. This procedure consistently elevates the intraocular pressure 1.5 times above normal in the animals.

The IOP of both eyes of each rat is measured using a Tonopen XL Tonometer before the surgery and once per week after the surgery. The average of ten measurements of the IOP are obtained for each eye.

The animals are allowed to survive for 2, 4 or 8 weeks after the first laser with six animals in each time point. One week before sacrifice, 6% Fluoro-Gold (FG) will be applied on the surface of both superior colliculi after removal of the overlying cortex. FG is taken up by the axon terminals of the retinal ganglion cells (RGCs) and is transported retrogradely to the somata in both retinas.

At the appropriate survival time, the animals are sacrificed with an overdose of xylazine/ketamine mixture. The eyes are enucleated and fixed in 4% paraformaldehyde for 60 minutes. Whole-mounted retinas are prepared and the FG labelled RGCs are counted using a fluorescence microscope. The RGCs are counted under an eyepiece grid (200×200 µm) at 500 µm intervals along the median line of each quadrant from the optic disc to the peripheral border of the retinas. The average density of the RGCs is calculated for the entire retina, the central retina (1-1.5 mm from optic disc) and peripheral retina (3.5-4 mm from the optic disc). The changes in the densities of RGCs are expressed as percent loss of RGCs comparing the laser treated and contralateral, control eye from the same animal.

The results show that there is about 13%, 21% and 25% loss of RGCs in the two, four and eight weeks' animals, respectively. Thus, we have produced a chronic glaucoma model in rats with consistent death of RGCs.

Glaucoma Treated with Lithium Chloride or Photosensitive Lithium Compounds

Glaucoma of the right eye was induced and the animals receive intraperitoneal injections of Lithium (LiCl, Sigma, St. Louis, USA; 85 µg/kg in sterile water), or Lithium Complex (1) (63.5 or 6.35 mg/kg which is equivalent to 85 or 8.5 µg/kg LiCl, in 2 mL Sigma C5135 Cremophor, 1 mL ethanol and 36 mL sterile water) twice daily for up to 14 days. The animals are sacrificed at 14 days (n=8 per group). The glaucoma and control retinas are removed at the appropriate survival times and processed for the three methods described above. Earlier time points are used if necessary.

Mechanism of Cell Death of Retinal Ganglion Cells

In order to study if apoptosis is the major mechanism of cell death in the glaucoma model, and whether Li would block apoptosis, TUNEL method, DAPI nuclear staining and Cleaved Caspase-3 immunohistochemistry are used to quantitatively assess apoptosis of RGCs. Rats with the right eye induced for glaucoma are prepared as above. In order to study the early events after laser photocoagulation, the animals are allowed to survive for 2, 4, 8 and 14 days (n=3 for each time point per group) after the first laser. At the appropriate survival time, the animals are perfused and both eyes are removed and prepared for paraffin embedding. Radial serial sections (5 µm) of the retina are obtained and adjacent sections are processed for TUNEL, DAPI nuclear staining and Cleaved Capase-3 immunihistochemistry. The results show that many cells undergo apoptosis in the retinal ganglion cells layer in a time-dependent manner with more apoptotic cells observed at later time points.

REFERENCES

1. Alward M, Driscoll C M And Weber S G, "Photochemical Control Of Metal-Ion Binding", 216th ACS National Meeting, Boston (1998)
2. Birch N J, *Uses Of Inorganic Chemistry In Medicine* Ed: Farrell, N. P. Cambridge, The Royal Society Of Chemistry (1999) pp. 11-25.
3. Birch N J, "Inorganic Pharmacology Of Lithium" *Chem. Rev.* (1999) Vol. 99, pp. 1659-2682.
4. Blank M, Soo L M, Wassermann N H And Erlanger B F, "Photoregulated Ion Binding" *Science* (1981) Vol. 214, pp. 70-72.
5. Cheung Z H, So K F, Lu Q, Yip H K, Wu W, Shan J J, Pang P K And Chen C F, "Enhanced Survival And Regeneration Of Axotomized Retinal Ganglion Cells By A Mixture Of Herbal Extracts" *J. Neurotrauma* (2002) Vol. 19, pp. 369-378.
6. Cho K S, Chan P M, So K F, Yip H K And Chung S K, "Ciliary Neurotrophic Factor Promotes The Regrowth Capacity But Not The Survival Of Intraorbitally Axotomized Retinal Ganglion Cells In Adult Hamsters" *Neuroscience* (1999) Vol. 34, pp. 623-628.
7. Cho K S, Chung S K, Yip H K And So K F, "Differential Effects Of Intravitreal Optic Nerve And Sciatic Nerve Grafts On The Survival Of Retinal Ganglion Cells And The Regeneration Of Their Axons" *J. Neurocytol.* (2001) Vol. 30, pp. 983-991.
8. Fan M, Yu L, Ming Y, Meng X And Zhao W, CN Patent 1158882 (1997).
9. Garcia-Valenzuela E, Shareef S, Walsh J And Sharma S, "Programmed Cell Death Of Retinal Ganglion Cells During Experimental Glaucoma" *Exp. Eye Res.* (1995) Vol. 61, pp. 33-44.
10. Ikeda T, Tsutsumi O And Wu Y, "Optical Switching And Image Storage By Means Of Photochromic Liquid Crystals" *Mol. Cryst. Liq. Cryst. Sci. Technol., Sect. A* (2000) Vol. 347, pp. 1-13.
11. Ishige S, Saeki K And Usui H, U.S. Pat. No. 4,220,356 (1980).
12. Ji J Z, "Signaling Pathways And Neuroprotection Of Retina Ganglion Cells In A Rat Glaucoma Model" (2002) The University of Hong Kong, Hong Kong.
13. Ji J Z, Elyaman W, Yip H K, Lee V W, Yick L W, Hugon J And So K F, "CNTF Promotes Survival Of Retinal Ganglion Cells After Induction Of Ocular Hypertension In Rats: The Possible Involvement Of STAT3 Pathway" *Eur. J. Neurosci* (2004) Vol. 19, pp. 265-272.
14. Laquis S, Chaudhary P And Sharma S, "The Patterns Of Retinal Ganglion Cell Death In Hypertensive" Eyes *Brain Res* (1998) Vol. 784, pp. 100-104.
15. Leske M C, "The Epidemiology Of Open-Angle Glaucoma: A Review" *Am. J. Epidemiol.* (1983) Vol. 118, pp. 166-191.
16. Levy D, "Recent Applications Of Photochromic Sol-Gel Materials" *Mol. Cryst. Liq. Cryst. Sci. Technol., Sect. A* (1997) Vol. 297, pp. 31-39.
17. Loerincz E, Szarvas G, Koppa P, Ujhelyi F, Erdei G, Sueto A, Varhegyi P, Sajti S, Kerekes A, Ujvari T And Ramanujam P S, "Polarization Holographic Data Storage Using Azobenzene Polyester As Storage Material" *Proceedings Of SPIE—The International Society For Optical Engineering* (2003) Vol. 4991, pp. 34-44.
18. Lu Q, Cui Q, Yip H K And So K F, "c-Jun Expression In Surviving And Regenerating Retinal Ganglion Cells: Effects Of Intravitreal Neurotrophic Supply" *Invest. Opthalmol. Vis. Sci.* (2003) Vol. 44, pp. 5342-5348.
19. Matsui F, Taniguchi H, Yokoyama Y, Sugiyama K And Kurita Y. "Application Of Photochromic 5-Dimethylaminoindolylfulgide To Photon-Mode Erasable Optical Memory Media With Non-Destructive Readout Ability Based On Wavelength Dependence Of Bleaching Quantum Yield" *Chem. Lett.* (1994) pp. 1869-1872.
20. Mckinnon S J, Lehman D M, Tahzib N G, Ransom N L, Reitsamer H A, Liston P, Lacasse E, Li Q, Korneluk R G And Hauswirth W W, "Baculoviral IAP Repeat-Containing-4 Protects Optic Nerve Axons In A Rat Glaucoma Model" *Mol. Ther.* (2002) Vol. 5, pp. 780-787.
21. Mittag T W, Danias J, Pohorenec G, Yuan H M, Burakgazi E, Chalmers-Redman R, Podos S M And Tatton W G, "Retinal Damage After 3 To 4 Months Of Elevated Intraocular Pressure In A Rat Glaucoma Model" *Invest. Opthalmol. Vis. Sci.* (2000) Vol. 41, pp. 3451-3459.
22. Morrison J, Moore C, Deppmeier L, Gold B, Meshul C And Johnson E, "A Rat Model Of Chronic Pressure-Induced Optic Nerve Damage" *Exp. Eye Res.* (1997) Vol. 64, pp. 85-96.
23. Natansohn A And Rochon P, "Photoinduced Motions In Azobenzene-Based Amorphous Polymers; Possible Photonic Devices" *Adv. Mater.* (1999) Vol. 11, pp. 1387-1391.
24. Nunzi J M, Charra F, Delysse S, Lefin P And Pfeffer N, "Limits Of Use Of Polymer Thin-Films For Spatial Light Modulation" *Proceedings Of SPIE—The International Society For Optical Engineering* (1996) Vol. 2969, pp. 138-144.
25. Osborne N N, Wood J P, Chidlow G, Bae J H, Melena J And Nash M S, "Ganglion Cell Death In Glaucoma: What Do We Really Know?" *Br. J. Opthalmol* (1999) Vol. 83, pp. 980-986.
26. Quigley H A And Green W R, "The Histology Of Human Glaucoma Cupping And Optic Nerve Damage: Clinicopathologic Correlation In 21 Eyes" *Opthalmology* (1979) Vol. 86, pp. 1803-1830.
27. Rompotis S, Parissi-Poulou M, Gikas E, Kazanis M, Vavayannis A And Panderi I, "Determination Of Valproic Acid In Human Plasma By HPLC With Fluorescence Detection" *J. Liq. Chromatogr. Related Technol.* (2002) Vol. 25, pp. 2833-2847.
28. Sawada A And Neufeld A, "Confirmation Of The Rat Model Of Chronic Moderately Elevated Intraocular Pressure" *Exp. Eye Res.* (1999) Vol. 69, pp. 525-531.
29. Shanzer A, Samuel D And Korenstein R, "Lipophilic Lithium Ion Carriers" *J. Am. Chem. Soc.* (1983) Vol. 105, pp. 3815-3818.
30. Shinbo K, Baba A, Kaneko F, Kato T, Kato K, Advincula R C And Knoll W, "In Situ Investigations On The Preparations Of Layer-By-Layer Films Containing Azobenzene And Applications For LC Display Devices" *Mater. Sci. Eng.* (2002) Vol. C22, pp. 319-325.
31. Shinkai S, Nakaji T, Nishida Y, Ogawa T And Manabe O, "Photoresponsive Crown Ethers 1. Cis-Trans Isomerism Of Azobenzene As A Tool To Enforce Conformational Changes Of Crown Ethers And Polymers" *J. Am. Chem. Soc.* (1980) Vol. 102. pp. 5860-5865.
32. Shinkai S, Nakaji T, Ogawa T, Shigematsu K And Manabe O, "Photoresponsive Crown Ethers 2. Photocontrol Of Ion Extraction And Ion Transport By A Bis (Crown Ether) With A Butterfly-Like Motion" *J. Am. Chem. Soc.* (1981) Vol. 103, pp. 111-115.
33. Siu, A. W., Leung, M. C. P., To, C. H., Siu, F. K. W., Ji, J. Z., And So, K-F, "Total Retinal Nitric Oxide Production Is Increased In Intraocular Pressure-Elevated Rats" *Experimental Eye Research* (2002) Vol. 75, pp. 401-406.
34. Stauffer M T, Knowles D B, Brennan C, Funderburk L, Lin F-T And Weber S G, "Optical Control Over Pb2+ Binding To A Crown Ether-Containing Chromene" *Chem. Commun.* (1997) pp. 287-288.
35. Ueda J, Sawaguchi S, Hanyu T, Yaoeda K, Fukuchi T, Abe H And Ozawa H, "Experimental Glaucoma Model In The Rat Induced By Laser Trabecular Photocoagulation After An Intracameral Injection Of India Ink" *Jpn. M. Opthalmol.* (1998) Vol. 42, pp. 337-344.
36. Woldemussie E, Ruiz G, Wijono M And Wheeler L A, "Neuroprotection Of Retinal Ganglion Cells By Brimonidine In Rats With Laser-Induced Chronic Ocular Hypertension" *Invest. Opthalmol. Vis. Sci.* (2001) Vol. 42, pp. 2849-2855.
37. Woldemussie E, Yoles E, Schwartz M, Ruiz G And Wheeler L A, "Neuroprotective Effect Of Memantine In Different Retinal Injury Models In Rats" *J. Glaucoma* (2002) Vol. 11, pp. 474-480.
38. Yoon H C, Shin H K, Kim C And Kwon Y S, "Fabrication Of Azobenzene-Terminated Dendrimers And Application To Photoswitching Devices" *Synth. Mat.* (2003) Vol. 137, pp. 1427-1428.
39. You S W, Bedi K S, Yip H K And So K F, "Axonal Regeneration Of Retinal Ganglion Cells After Optic Nerve Pre-Lesions And Attachment Of Normal Or Pre-Degenerated Peripheral Nerve Grafts" *Vis. Neurosci.* (2002) Vol. 19, pp. 661-668.
40. Zhang X H, Chen B J, Lin X Q, Wong O Y, Lee C S, Kwong H L, Lee S T And Wu S K, "A New Family Of Red Dopants Based On Chromene-Containing Compounds For Organic Electroluminescent Devices" *Chem. Mater.* (2001) Vol. 13, pp. 1565-1569.
41. Zhang Z, Burns D C, Kumita J R, Smart O S And Woolley G A, "A Water-Soluble Azobenzene Cross-Linker For Photocontrol Of Peptide Conformation" *Bioconjugate Chem.* (2003) Vol. 14, pp. 824-829.

What is claimed is:

1. A method for protecting against the degeneration of retinal ganglion cells caused by an eye disease in a subject comprising:
(a) providing a photosensitive aza-crown ether or crown ether of a chromene or a diazene compound that releases lithium upon exposure to light;
(b) administering an effective amount of the aza-crown or crown ether of a chromene or a diazene compound in a pharmaceutically acceptable carrier to the eye of the subject; and
(c) exposing the eye of the subject to an external light source to cause the aza-crown ether or crown ether of a chromene or a diazene compound to release lithium wherein the photosensitive aza-crown ether or crown ether moiety of a chromene or diazene compound has one of the following structures:

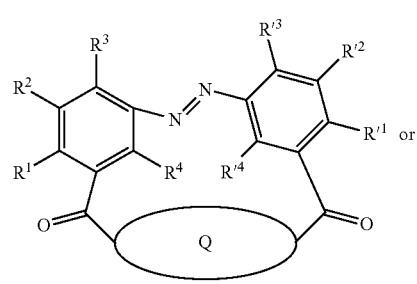

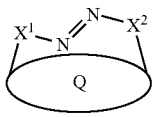

wherein Q is a crown ether or an aza-crown ether;
wherein R1, R2, R3, R'1, R'2, and R'3, are the same or different, and are each a phenyl ring or a substituted phenyl ring, a hydrogen; a halogen, a hydroxyl group, an unsubstituted or substituted lower alkyl, cycloalkyl, aryl, acyl, alkoxy, acylamino, aralkyl, cyanocarboxyl, thio, vinyl, stryryl, alkoxycarbonyl, carbamoyl, aminocarbonyl, or phenoxycarbonyl; and
wherein X1 and X2 are each a phenyl ring or a substituted phenyl ring, an unsubstituted or substituted lower alkyl, cycloalkyl, aryl, acyl, alkoxyl, aclyamino, aralkyl, cyanocarboxyl, thio, vinyl, stryryl, alkoxycarbonyl, carbamoyl, aminocarbonyl, or phenoxycarbonyl.

2. A method according to claim 1, wherein the eye disease is glaucoma.

3. A method for protecting against the degeneration of retinal ganglion cells caused by an eye disease in a subject comprising:
(a) providing an effective amount of a photosensitive aza-crown ether or crown ether of a chromene or a diazene compound that releases lithium upon exposure to light;
(b) administering the aza-crown or crown ether of a chromene or a diazene compound in a pharmaceutically acceptable carrier to the eye of the subject; and
(c) exposing the eye of the subject to an external light source to cause the aza-crown ether or crown ether of a chromene or a diazene compound to release lithium wherein the photosensitive aza-crown ether or crown ether moiety of a chromene or diazene compound has one of the following structures:

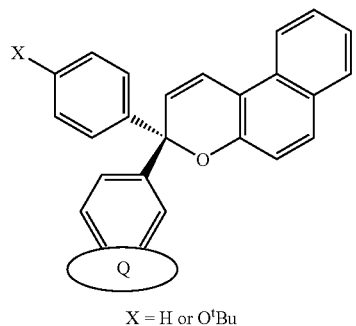

X = H or O$^t$Bu wherein Q is a crown ether or an aza-crown ether;
wherein R1, R2, R3, R'1, R'2, and R'3, are the same or different, and are each a phenyl ring or a substituted phenyl ring, a hydrogen; a halogen, a hydroxyl group, an unsubstituted or substituted lower alkyl, cycloalkyl, aryl, acyl, alkoxy, acylamino, aralkyl, cyanocarboxyl, thio, vinyl, stryryl, alkoxycarbonyl, carbamoyl, aminocarbonyl, or phenoxycarbonyl; and
wherein X1 and X2 are each a phenyl ring or a substituted phenyl ring, an unsubstituted or substituted lower alkyl, cycloalkyl, aryl, acyl, alkoxy, aclyamino, aralkyl, cyanocarboxyl, thio, vinyl, stryryl, alkoxycarbonyl, carbamoyl, aminocarbonyl, or phenoxycarbonyl, and
wherein the compound that releases lithium upon exposure to light is administered by introducing said compound into a patient's bloodstream.

4. A method according to claim 1, wherein the lithium ion is chelated to a crown ether or aza-crown ether moiety to form a chelated lithium compound that releases a lithium ion upon exposure to light.

5. A method according to claim 1, wherein the lithium ion is reversibly bound to a diazene or chromene compound through a crown ether or aza-crown ether moiety forming a lithium ion releasing chromene or diazene compound, whereby the lithium ion is released upon exposure of the eye of the subject to light.

6. A method for treatment of glaucoma comprising reversibly binding lithium to a diazene or chromene bridge crown ether compound to obtain a prodrug, administering an amount of the prodrug effective to treat glaucoma in a pharmaceutically acceptable vehicle to an eye of a patient needing such treatment, and exposing the eye of the patient to an external light source to release the lithium to the eye of the patient; wherein the compound has one of the following structures:

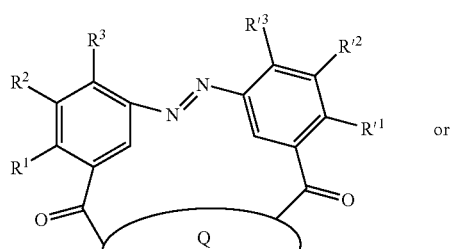

or

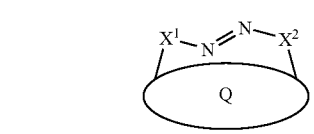

wherein Q is a crown ether or an aza-crown ether;
wherein R1, R2, R3, R'1, R'2, and R'3, are the same or different, and are each a phenyl ring or a substituted phenyl ring, a hydrogen; a halogen, a hydroxyl group, an unsubstituted or substituted lower alkyl, cycloalkyl, aryl, acyl, alkoxy, acylamino, aralkyl, cyanocarboxyl, thio, vinyl, stryryl, alkoxycarbonyl, carbamoyl, aminocarbonyl, or phenoxycarbonyl; and
wherein X1 and X2 are each a phenyl ring, or a substituted phenyl ring, an unsubstituted or substituted lower alkyl, cycloalkyl, aryl, acyl, alkoxy, aclyamino, aralkyl, cyanocarboxyl, thio, vinyl, stryryl, alkoxycarbonyl, carbamoyl, aminocarbonyl, or phenoxycarbonyl.

7. A method for treatment of glaucoma comprising reversibly binding lithium to a diazene or chromene bridge crown ether compound to obtain a prodrug, administering an effective amount of the prodrug to treat glaucoma in a pharmaceutically acceptable vehicle to the eye of a patient needing such treatment, and exposing the eye of the patient to art external light source to release the lithium to the eye of the patient , wherein the compound has the following structure:

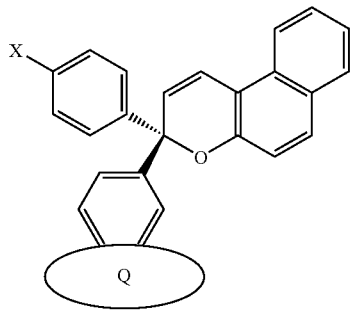

wherein Q is a crown ether or aza-crown ether and X is H or t-butoxy.

8. A method for protecting against the degeneration of retinal ganglion cells caused by art eye disease in a subject comprising:

reversibly binding lithium to a diazene or chromene bridge crown ether compound to obtain a prodrug, administering an effective amount of the prodrug in a pharmaceutically acceptable vehicle to protect against degeneration of retinal ganglion cells to an eye of a patient needing such treatment, and exposing the eye of the patient to an external light source to release the lithium to the eye of the patient; wherein the compound has the following structure:

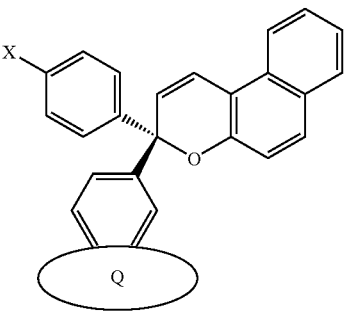

wherein Q is a crown ether or aza-crown ether and X is H or t-butoxy.

* * * * *